United States Patent
Pinna

[19]

[11] Patent Number: 5,595,564
[45] Date of Patent: Jan. 21, 1997

[54] DEVICE FOR RETARDING HAIR LOSS AND FOR STIMULATING ITS REGROWTH

[75] Inventor: Marco Pinna, Induno Olona, Italy

[73] Assignee: Biofarm S.R.L., Milan, Italy

[21] Appl. No.: 344,692

[22] Filed: Nov. 18, 1994

[30] Foreign Application Priority Data

Nov. 26, 1993 [IT] Italy .................. MI932505 U

[51] Int. Cl.$^6$ .................................................. A61N 1/00
[52] U.S. Cl. ................................. 600/14; 600/15
[58] Field of Search ................................ 600/9–15

[56] References Cited

U.S. PATENT DOCUMENTS

| | | | |
|---|---|---|---|
| 5,116,304 | 5/1992 | Cadwell | 600/13 |
| 5,415,617 | 5/1995 | Kraus | 600/13 |

FOREIGN PATENT DOCUMENTS

| | | | |
|---|---|---|---|
| 0497672 | 8/1992 | European Pat. Off. | |
| 1350890 | 12/1963 | France. | |
| 6170003 | 6/1994 | Japan | 600/9 |
| 2262043 | 6/1993 | United Kingdom. | |
| 2261820 | 6/1993 | United Kingdom | 600/13 |

OTHER PUBLICATIONS

Maddin, Stuart W., "Electrotrichogenesis: Further Evidence Of Efficacy and Safety on Extended Use", *International Journal of Dermatology*. vol. 31, No. 12, Dec. 1992, pp. 878–880.

Maddin, Stuart W., "The Biological Effects of a Pulsed Electrostatic Field with Specific Reference to Hair", *International Journal of Dermatology*. vol. 29, No. 6, Jul.–Aug. 1990, pp. 446–450.

*Primary Examiner*—Angela D. Sykes
*Assistant Examiner*—John Lacyk
*Attorney, Agent, or Firm*—Oblon, Spivak, McClelland, Maier & Neustadt, P.C.

[57] ABSTRACT

A device for retarding hair loss and for stimulating its regrowth comprising an electrical pulse generator (3, 4) connected to at least one electrically conducting cable (2, 20) extending within a shaped structure to be applied to a person's skull.

5 Claims, 2 Drawing Sheets

DEVICE FOR RETARDING HAIR LOSS AND FOR STIMULATING ITS REGROWTH

BACKGROUND OF THE INVENTION

1. Field of the Invention

This invention relates to a device for retarding hair loss and for stimulating its regrowth.

DISCUSSION OF THE BACKGROUND

Devices of the aforesaid type are known comprising one or more moving members for mechanically massaging the scalp and in particular those parts of the head where hair loss is greatest.

Satisfactory retarding of hair loss cannot be obtained with known devices.

Moreover these devices are uncomfortable to handle, they are relatively heavy and are tiring to use as they have to be held in contact with the head for relatively long periods.

Apparatus have recently been proposed which have proved of some interest in retarding hair loss and stimulating its growth, such apparatus using pulsating electrostatic fields (see for example the articles by W. Stuart Maddin published in the International Journal of Dermatology, July-August '90, vol. 29 No 12, and December '92, vol. 31, No. 12). These apparatus comprised helmet provided with electrically conducting plates connected to large pulsating electrostatic field generators.

Although the impedance of the output circuit of this apparatus is so high as to limit the delivered current to a value which is completely harmless even if the scalp makes direct contact with the plates, this does not eliminate the unpleasant and dangerous effect deriving therefrom. It is also difficult to adjust the depth of action of the electrostatic field, consequently requiring a relatively complicated and costly regulator circuit. The electrostatic apparatus of the aforesaid type also has a very low maximum energy efficiency when powered by 12 volt batteries or the like, this voltage being converted into a much higher voltage to achieve the desired results.

SUMMARY OF THE INVENTION

An object of the present invention is to provide a device of the aforesaid type which is easy and comfortable to use without risk, is of small overall size, is easily adjustable by a normal user, and in particular is effective in retarding hair loss and stimulating its regrowth.

A further object is to provide a low-cost device of simple construction.

These and further objects which will be apparent to an expert of the art are attained by a device in accordance with the accompanying claims.

BRIEF DESCRIPTION OF THE DRAWINGS

The present invention will be more apparent from the accompanying figures, which are provided by way of non-limiting example and in which.

DETAILED DESCRIPTION OF THE PREFERRED EMBODIMENTS

Figure 1:
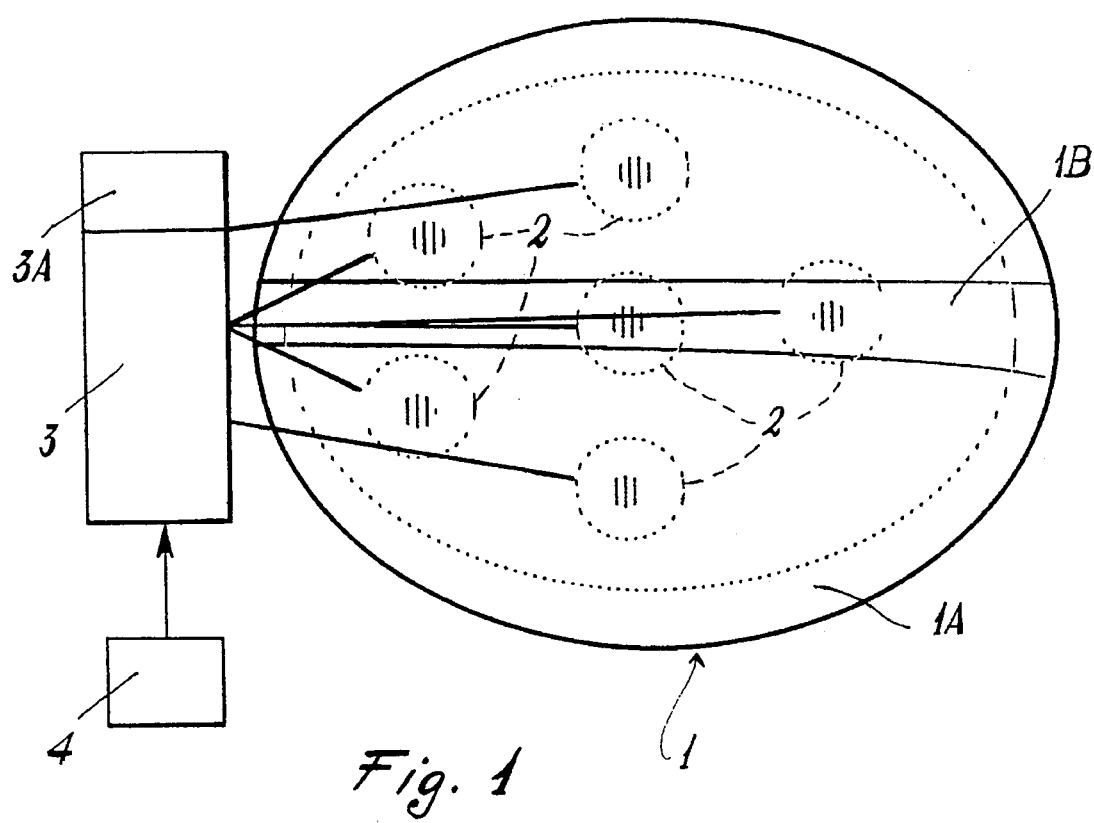
FIG. 1 is a schematic view of a first embodiment of the device.

FIG. 1 shows a support element 1 with which there are associated a plurality of electromagnetic wave generator elements 2 (six are shown in the example) connected electrically to a regulator member 3 and a powering member 4.

In the illustrated embodiment the support element 1 is in the form of a helmet or hat (in the figure it is shown in schematic view from above) and comprises two stiffening parts 1A, 1B.

The hat 1 is formed for example of plastics material or fabric, and comprises a plurality of seats (not shown) for housing and retaining the generators. These latter consist for example of a cable arranged in "daisy" loops.

The powering member 4 can be a usual battery or a usual plug for connecting the device to the electric mains.

The regulator member 3 is of conventional type for the expert of the art and will not be described in detail.

Depending on the type of power supply and generators 2, the member 3 is arranged to feed the generators with power such as to generate waves having an intensity of at least 1 gauss in proximity to the generators.

The regulator member 3 also comprises a conventional interface 3A by which the user can set the desired frequency and intensity. Using the interface 3A the user can also choose the type of electromagnetic wave, which can for example be sinusoidal or semisinusoidal, trapezoidal, triangular, periodic or in trains of adjustable length and frequency, or in waves which alternate at adjustable frequency.

It should be noted that the regulator member 3 and powering member 4 could advantageously be combined into a single component. The regulator member could also comprise a usual programmable electronic circuit, for example of the microprocessor type, for powering the generators 2 such as to generate a periodic sequence of electromagnetic waves of preset variable intensity, frequency and type. In this manner it is possible to program, for a set period for example of thirty minutes, an electromagnetic wave sequence for example of the following type: for the first ten minutes continuous sinusoidal waves at 50 hertz and 4 gauss, for the next ten minutes triangular waves at 40 hertz and 3 gauss lasting one minute followed by a 30 second pause, and for the last ten minutes waves as for the first ten minutes.

Advantageously said circuit is programmed by the device manufacturer such that the user is able only to turn the device on and off, hence simplifying the use of the device. The circuit could also contain different preset electromagnetic wave sequences according to user problems. The circuit could also be of the type for memorizing a user sequence of electromagnetic waves.

It has been found experimentally that the useful frequency and intensity of the electromagnetic waves generated by the generators range from 10 to 100 hertz and from 1 to 100 gauss respectively.

The device has been tested on persons with hair loss problems and baldness. After only a short treatment period (a few days) most of the persons subjected to the test showed a decrease in hair loss and, in the case of some persons, a partial regrowth of hair in the regions from which it had been lost.

A modification (not shown) to the aforedescribed embodiment comprises an element for supporting a structure grippable by the user and carrying one or more generators.

In this case the user can concentrate the electromagnetic action onto a particular region of the scalp. The regulator and powering members could then be housed in said grippable structure or be connected to it by a cable.

Figure 2:
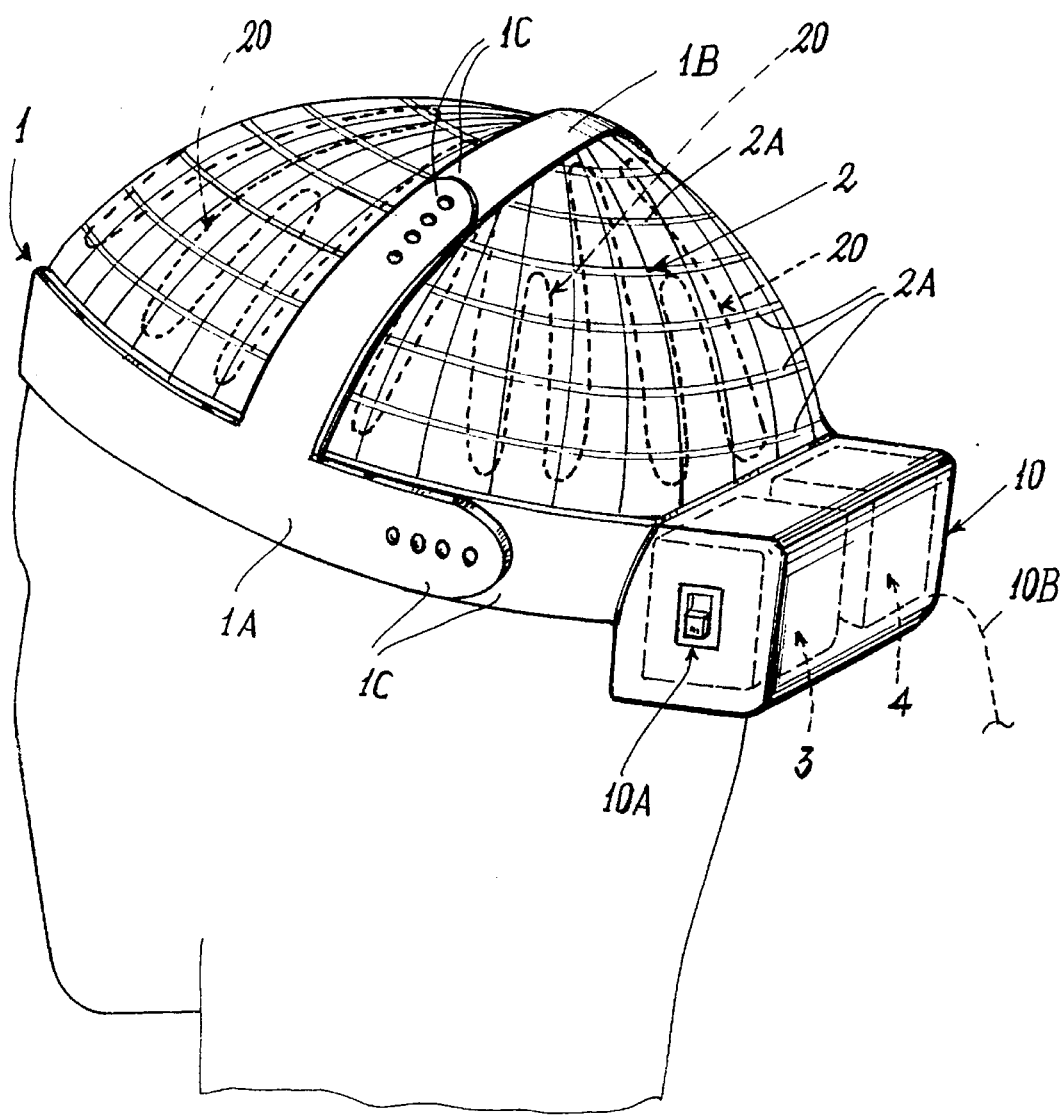
FIG. 2 is a schematic view of a second embodiment.

FIG. 2 shows a second embodiment (those elements in common with the aforedescribed embodiment being indicated by the same reference numerals) comprising a single generator in the form for example of a conventional flexible electric cable wound into a plurality of turns 2A and associated with the support element 1 for example by sewing.

A container 10 for the regulator member 3 and powering member 4 is connected to the stiffening part 1A of the element 1 and comprises a usual switch 10A for switching on the device.

Instead of the simple switch 10A the container 10 can comprise, if necessary, an interface 3A (not shown) similar to the preceding.

The regulator member 3 is advantageously of the aforedescribed programmable type. The powering member 4 can be a battery or a simple electric cable 10B for connection to the domestic electricity supply.

Advantageously the stiffening parts 1A, 1B can be lengthened or shortened to adjust the size of the hat-shaped support element 1 to the size of the user's head. For this purpose each of the two parts 1A, B comprises, for example, portions 1C which can be snap-connected together in conventional manner.

In a further preferred embodiment (for simplicity shown only partly by dashed lines on FIG. 2), with the inner face of a structure shaped in the form of a helmet or head cover there is associated a single electric cable arranged starting from the centre of the helmet in such a manner as to form a plurality of loops or lobes 20. In each lobe the cable is arranged so that it returns about itself so that the magnetic field generated by a part of the cable is partly nullified by the field generated by that cable part adjacent to it.

The cable associated with the helmet is connected to an electronic circuit arranged to generate a sequence of current pulses for example of 2 milliseconds duration at a frequency of fifty pulses per second. The intensity of these pulses is such that the cable associated with the electronic circuit generates an electromagnetic field with an intensity of about 2 gauss in proximity to the cable and of negligible intensity at about 5 millimeters therefrom.

The electronic circuit for generating the current pulses is of conventional type to the expert of the art and is therefore not described in detail hereinafter, it being sufficient to note that it is advantageously of microprocessor type powered by a usual battery, for example of twelve volts, via a usual voltage stabilizer circuit, and is connected to a usual power circuit connected to the cable within the helmet, all these being within the scope of an expert of the art as stated.

Advantageously the electronic circuit is activated by pushing a pushbutton switch, and is deactivated automatically after a predetermined adjustable time period, for example thirty minutes.

Because of the particular lobe arrangement of the electric cable generating the magnetic field and the limited intensity of this latter, it has been found that the magnetic field acts only on the scalp so as not to stimulate those parts of the body not concerned with the application and not waste energy, hence without creating any danger for the user. Moreover in this manner a magnetic field is obtained which is distributed uniformly over the entire skull and extends for only a few millimeters from the conductor.

Preferably the lobes 20 of the electric cable generating the electromagnetic field are inserted into plastic bags (not shown) inflatable manually by the helmet user using a conventional pump associated with the helmet. The cable can adhere internally to that face of the bag which comes into contact with the scalp. In this manner the electric cable emitting the magnetic field is always in contact with the scalp, even for varying user skull dimensions.

Finally it should be noted that the illustrated embodiments are given by way of example only, and that numerous modifications are possible all falling within the same inventive concept.

I claim:

1. A device for retarding hair loss and for stimulating its regrowth, comprising:
    an electrical pulse generator connected to an electrically conducting cable extending within a shaped structure to be applied to a person's skull, said cable being distributed in the form of loops, said generator providing to said cable electrical pulses for generating a pulsating electromagnetic field around said cable having an intensity of at least one gauss in proximity to the conducting cable, and wherein the intensity of said field is essentially negligible at approximately 5 mm from a surface of said conducting cable.

2. A device as claimed in claim 1, wherein said electrical pulses have a duration of about 2 milliseconds and are repeated with a frequency of about fifty pulses per second.

3. A device as claimed in claim 1, wherein the surface of said conducting cable (20) which is to face the user's skull is protected by a plastic film.

4. A device as claimed in claim 3, further comprising a sealed plastic bag enclosing said conducting cable.

5. A device as claimed in claim 4, further comprising a pump connected to said bag for inflating said bag.

* * * * *

UNITED STATES PATENT AND TRADEMARK OFFICE
CERTIFICATE OF CORRECTION

PATENT NO. : 5,595,564
DATED : January 21, 1997
INVENTOR(S) : Marco PINNA

It is certified that error appears in the above-indentified patent and that said Letters Patent is hereby corrected as shown below:

On the title page, in Item [30], the Foreign Application Priority Data is incorrect. It should read:

-- [30]

Nov. 26, 1993   [IT]  Italy..............MI93A2505. --

Signed and Sealed this

Twenty-ninth Day of April, 1997

Attest:

BRUCE LEHMAN

Attesting Officer

Commissioner of Patents and Trademarks